United States Patent [19]

Hahn

[11] 4,108,832
[45] Aug. 22, 1978

[54] SILACYCLOPENTYL-BIS-EPSILON-CAPROLACTAM

[75] Inventor: James R. Hahn, Midland, Mich.

[73] Assignee: Dow Corning Corporation, Midland, Mich.

[21] Appl. No.: 743,820

[22] Filed: Nov. 22, 1976

Related U.S. Application Data

[62] Division of Ser. No. 644,379, Dec. 29, 1975, Pat. No. 4,012,375.

[51] Int. Cl.$^2$ .............................................. C08G 77/04
[52] U.S. Cl. ........................................ 528/32; 528/38
[58] Field of Search ..................... 260/46.5 E, 46.5 G

[56] References Cited

U.S. PATENT DOCUMENTS

| | | | |
|---|---|---|---|
| 2,876,209 | 3/1959 | de Beaneville et al. | 260/45.4 |
| 2,876,234 | 3/1959 | Hurwitz et al. | 260/326.5 |
| 3,378,520 | 4/1968 | Sattlegger et al. | 260/46.5 G |
| 3,417,047 | 12/1968 | Golitz et al. | 260/46.5 G |
| 3,509,191 | 4/1970 | Atwell | 260/448.2 |
| 4,012,375 | 3/1977 | Hahn | 260/239.3 R |

Primary Examiner—Melvyn I. Marquis
Attorney, Agent, or Firm—Roger H. Borrousch

[57] ABSTRACT

Silacyclopentyl-bis-epsilon-caprolactam,

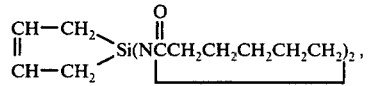

is useful as a chain extender for hydroxyl compounds, especially hydroxyl endblocked polydimethylsiloxanes.

1 Claim, No Drawings

SILACYCLOPENTYL-BIS-EPSILON-CAPROLACTAM

This is a division of application Ser. No. 644,379, filed Dec. 29, 1975, now U.S. Pat. No. 4,012,375.

BACKGROUND OF THE INVENTION

1. Field of the Invention

This invention relates to a silacyclopentene.

2. Description of the Prior Art

Silacyclopentenes are shown by Atwell in U.S. Pat. No. 3,509,191, where he discloses dichlorosilacyclopentene which is a precursor for the preparation of the silacyclopentenyl-bis-epsilon-caprolactam of the present invention.

Silicon bonded lactams are known from Hurwitz and de Benneville in U.S. Pat. No. 2,876,209 and U.S. Pat. No. 2,876,234. Hurwitz and de Benneville describe silanes containing the lactam group where the generic formula is

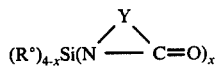

in which R° is a cyclohexyl group, an aryl group, an alkenyl group or an alkyl group having 1 to 18 carbon atoms, Y is an alkylene group having 3 to 18 carbon atoms with a chain of at least 3 but no more than 5 carbon atoms extending between the N atom and carbonyl group, and x is an integer having a value of 1 to 4. Hurwitz and de Benneville describe the preparation of these lactams by reacting a lactam having a reactive hydrogen with a chlorosilane in the presence of an acid acceptor such as a tertiary amine at room temperature or below, preferably in an anhydrous solvent. U.S. Pat. No. 2,876,234 is hereby incorporated by reference to show the preparation of the lactam silicon bond.

SUMMARY OF THE INVENTION

Silacyclopentenyl-bis-epsilon-caprolactam is useful as a chain extender for hydroxyl endblocked polydimethylsiloxanes as well as other hydroxyl functional compounds.

DESCRIPTION OF THE INVENTION

This invention relates to silacyclopentenyl-bis-epsilon-caprolactam,

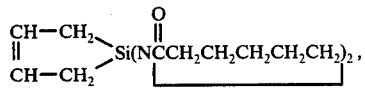

The above formula is representative of a particular species of silacyclopentenyl-bis-epsilon-caprolactam. However, the present invention also includes the isomer of the formula

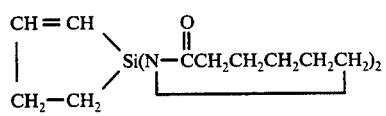

The preparation of the silacyclopentenyl group usually results in a mixture of both isomers. Mixtures of the isomers are also included in the present invention.

The best method for preparing the silacyclopentenyl-bis-epsilon-caprolactam is mixing under substantially anhydrous conditions dichlorosilacyclopentene, epsilon-caprolactam in the presence of triethylamine and toluene at room temperature.

Silacyclopentenyl-bis-epsilon-caprolactam is a very fast chain extender and will increase the molecular weight of a hydroxyl endblocked polydimethylsiloxane fluid to a gum in a matter of seconds when stoichiometric amounts of hydroxyl groups to epsilon-caprolactam groups are used. When the amount of silacyclopentenyl-bis-epsilon-caprolactam is in excess the reaction is slower and requires the presence of moisture (water) to chain extend. The resulting chain extended polymers will contain spaced silacyclopentenyl units along the chain which can be used in the same manner as vinyl radicals in making elastomers such as by using vinyl specific peroxides or by using siloxane compounds containing silicon-bonded hydrogen atoms and a platinum catalyst.

The following example is presented for illustrative purposes only and should not be construed as limiting the present invention which is delineated in the claims.

EXAMPLE

In a one liter 3-necked flask equipped with a stirrer, Dean Stark trap and condenser, 95 g. of epsilon-caprolactam, 101 g. of triethylamine and 600 ml. of toluene was placed and the mixture was azeotroped to dry the reactants. The dried mixture was cooled and 0.4 mol of dichlorosilacyclopentene was added over a 10 minute period. The mixture was stirred for 2.5 hours and then filtered under nitrogen. The filter cake was washed with 200 ml. of dry toluene. The resulting solution was vacuum distilled to remove the toluene which left a residue of silacyclopentenyl-bis-epsilon-caprolactam (crude), then the crude silacyclopentenyl-bis-epsilon-caprolactam was vacuum distilled. The silacyclopentenyl-bis-epsilon-caprolactam had a boiling point of 169° C at 0.087 Pa.

A mixture of 0.4 g. of crude silacyclopentenyl-bis-epsilon-caprolactam and 10 g. of a hydroxyl endblocked polydimethylsiloxane having a viscosity at 25° C. of 4.5 Pa.s skinned over in 1 minute when exposed to the atmosphere. The distilled product skinned over in the same time when 0.44 g. was mixed with 10 g. of the hydroxyl endblocked polydimethylsiloxane. A stoichiometric amount of silacyclopentenyl-bis-epsilon-caprolactam with the hydroxyl endblocked polydimethylsiloxane reacted so rapidly and increased in molecular weight so rapidly that the mixing could not be completed as thoroughly as desired. Mixing stoichiometric amounts of methylvinyldi-(N-methylacetamido)-silane with the hydroxyl endblocked polydimethylsiloxane did not increase to a viscosity of 1000 Pa.s in 20 minutes.

That which is claimed is:

1. A method of increasing the molecular weight of an organosiloxane having silicon-bonded hydroxyl radicals comprising mixing silacyclopentenyl-bis-epsilon-caprolactam and the organosiloxane.